(12) United States Patent
Tharp

(10) Patent No.: US 11,712,699 B2
(45) Date of Patent: Aug. 1, 2023

(54) CRYRO DEVICE AND METHOD FOR PROCESSING CANNABIS FLOWERS

(71) Applicant: Walter L Tharp, Encinitas, CA (US)

(72) Inventor: Walter L Tharp, Encinitas, CA (US)

( * ) Notice: Subject to any disclaimer, the term of this patent is extended or adjusted under 35 U.S.C. 154(b) by 0 days.

(21) Appl. No.: 16/595,359

(22) Filed: Oct. 7, 2019

(65) Prior Publication Data

US 2020/0108398 A1    Apr. 9, 2020

Related U.S. Application Data

(60) Provisional application No. 62/741,944, filed on Oct. 5, 2018.

(51) Int. Cl.
| | |
|---|---|
| *B02C 17/18* | (2006.01) |
| *A24B 1/04* | (2006.01) |
| *A24B 3/18* | (2006.01) |
| *A24B 15/18* | (2006.01) |
| *A61F 2/82* | (2013.01) |
| *A61F 2/962* | (2013.01) |
| *B02C 17/02* | (2006.01) |
| *B07B 1/22* | (2006.01) |
| *A01G 3/00* | (2006.01) |
| *A61F 2/95* | (2013.01) |
| *A61F 2/966* | (2013.01) |
| *A61F 2/24* | (2006.01) |

(52) U.S. Cl.
CPC ............ *B02C 17/1815* (2013.01); *A24B 1/04* (2013.01); *A24B 3/18* (2013.01); *A24B 15/18* (2013.01); *A61F 2/82* (2013.01); *A61F 2/962* (2013.01); *B02C 17/02* (2013.01); *B07B 1/22* (2013.01); *A01G 2003/005* (2013.01); *A01G 2003/007* (2013.01); *A61F 2002/9511* (2013.01)

(58) Field of Classification Search
CPC ..... B02C 17/1815; B02C 17/02; B02C 17/18; B02C 17/1885; B02C 17/1859; B02C 17/1857; A24B 15/18; A24B 1/04; A24B 3/18; A24B 5/06; A24B 5/16; A24B 5/00; B07B 1/22; A01G 2003/005; A01G 2003/007; A25B 15/28
See application file for complete search history.

(56) References Cited

U.S. PATENT DOCUMENTS

| | | | | |
|---|---|---|---|---|
| 3,283,944 | A | * | 11/1966 | Richardson ............. B24B 31/02 220/252 |
| 3,970,091 | A | * | 7/1976 | Banks ...................... A24B 5/06 131/313 |
| 2011/0168814 | A1 | * | 7/2011 | Brook-Levinson ......................... B02C 17/161 241/21 |
| 2018/0369716 | A1 | * | 12/2018 | Robbins ............. B01D 11/0207 |
| 2019/0153484 | A1 | * | 5/2019 | Bray ....................... C12P 5/007 |
| 2019/0218714 | A1 | * | 7/2019 | Oguchi ................ D21G 9/0027 |
| 2019/0297782 | A1 | * | 10/2019 | Mosman .................. A01G 3/00 |
| 2019/0299218 | A1 | * | 10/2019 | Camaren ................ B02C 17/02 |
| 2020/0022406 | A1 | * | 1/2020 | Grant ...................... B02C 23/10 |

* cited by examiner

*Primary Examiner* — Matthew Katcoff
*Assistant Examiner* — Mohammed S. Alawadi
(74) *Attorney, Agent, or Firm* — Doan K. Harms

(57) ABSTRACT

A device and method for cleaning flowers and buds of plants of leaves and plant matter and particulate is provided. The buds are cleaned within a rotating drum having openings in a circular sidewall which rotates adjacent jets emitting gas. Freezing of the plant material and concurrent impacts from ice crystals formed by emitting gas, cleans the buds and flowers of unwanted plant material and particulate.

15 Claims, 4 Drawing Sheets

CRYRO DEVICE AND METHOD FOR PROCESSING CANNABIS FLOWERS

This application claims priority to U.S. Provisional Patent Application Ser. No. 62/741,944 filed on Oct. 5, 2018. The disclosed device relate generally to a device and method for efficient processing of *cannabis* plants. More particularly, it relates to a rotating tumbling device employing extremely cold pressurized gas communicated through jets to a rotating mesh tumbler of buds or flowers to clean them of leaves and debris.

FIELD OF THE INVENTION

Background of the Invention

The trimming of buds and flowers from many crops of plants, is frequently done by hand to remove unwanted plant matter and particulate. For example, prior to embodiments of the disclosed invention herein, removing unwanted plant leaves, particulate and plant matter, from buds and flowers, involved the use of trimming implements and machines which employ a blade type cutting system. Such trimming is primarily accomplished by hand using trimmers and sharp implements which work best when cut at right angles.

It is well known however, that the most consistent results to remove the most leaves, plant matter and particulate, is accomplished by hand-trimming. Due to the number of people involved for such trimming in an industrial setting, this can be extremely costly in time and in wages for plant cultivators.

However, even where humans are employed with sharp implements such as scissors, in the attempt to produce consistent results in the cleaning process, it is a messy undertaking due to the sticky nature of the flowers and any plant or particulate matter being trimmed therefrom. In many instances, trimming components and machines are not only costly to maintain but, have to be serviced daily.

Further, even with sharp implements, and scores of employees hand-trimming the flowers and buds, it is hard for cultivators to maintain a high volume flow of cleaned product. This is primarily because employees become fatigued both physically and mentally during a shift of trimming. Additionally, their tools and their hands become sticky which tends to cause leaves and particulate to stick to them and to fall into trimmed material.

The device and method herein provides for the processing of flowers and buds from *cannabis* as well as other plants, in an enhanced and less time consuming endeavor. It also enhances the final product through the removal of more particulate and leaves than is conventionally possible by human and other trimmers.

The forgoing examples concerning trimming and cleaning of plant flowers or buds such as those from *cannabis* and other plants, and issues regarding such, are intended to be illustrative and not exclusive, and they do not imply any limitations on the invention described and claimed herein.

Various other limitations of the related art are known or will become apparent to those skilled in the art upon a reading and understanding of the specification below and the accompanying drawings.

SUMMARY OF THE INVENTION

The device herein provides a solution to the shortcomings of plant cultivators in the area of cleaning and trimming plant flowers and buds. Unlike conventional hand trimming, which is very time consuming and expensive, the device and method herein reduces the time required for such trimming and achieves superior results. This of course provides a significant reduction in operating costs and equally significant increase in production.

In the system herein, a cryo tumbler having a hopper and a rotatable drum with a mesh-like sidewall is connected to a pressurized supply of gas. In the method herein which employs pressurized gas communicated at very low temperatures to the tumbler, an extremely efficient method to trim leaves and remove particulate and plant matter from flowers of plants is provided.

The cryo tumbler device includes a rotating drum which is operatively mounted on an axle within a sealable hopper. The tumbler is formed of a circular mesh-like sidewall extending to an endwall which is currently solid or has no such openings. The sidewall of the tumbler has openings formed therein between ¼ inch to ⅜ inch in diameter with a currently preferred diameter of substantially inch. By substantially is meant plus or minus 20 percent.

A hopper surrounds the rotating drum and has an open position wherein the drum may be accessed for filling and employing of plant matter to be processed. A lid has an open position wherein such access to the drum is provided, and a closed position substantially sealing the internal cavity of the hopper in which the drum rotates. Preferably a thermocouple is arranged within the hopper.

Power to rotate the drum within the hopper is provided by an electric motor which may be adjusted for rotational speed with a controller to adjust the rotational speed of the drum when in use. Currently, a rotational speed of between substantially 30 to 90 revolutions a minute is preferred. Experimentation has shown that with the sidewall of the drum having the noted size openings therein, a rotation speed of substantially 60 RPM's is especially preferred for excellent results. By substantially is meant herein to be plus or minus 20 percent.

The variable speed drive motor is mounted on the hopper and mechanically coupled to the drum system using either chains, fan belts, or gearing, or combination thereof. A speed control is preferably provided to allow the user to fine tune the rotation speed to the crop being processed. Such speed controls are well known in the art, and allow the user to change the rotational speed of the drum. Further, a sensor may be employed to monitor drum speed and automatically change the motor speed to maintain the desired RPM's of the drum.

A plurality of gas injection jets are positioned within the interior cavity of the hopper and run substantially parallel to the surface of the sidewall of the rotating drum. The controller is preferably communicatively coupled to the variable speed drive motor, the thermocouple within the interior cavity, and the plurality of gas injection jets. The controller is programmed with software instructions to measure a temperature in the interior cavity of the hopper with the thermocouple or a similar temperature sensor. With the lid closed and substantially sealing the interior cavity, the controller will open valves from a pressurized gas supply to communicate gas in a substantially liquid state, into the interior cavity of the hopper to lower the temperature in the hopper until a desired temperature is reached.

Thereafter, gas will continuously communicate from the plurality of jets, and to the exterior of the sidewall of the rotating drum. The combination of extremely cold temperatures caused by the jet ejection of gas, and the impact of ice crystals formed by the interaction of the gas from the jets with air within the interior cavity, has a dual cleaning effect to the contents of the drum.

First, the extremely cold temperatures, currently −10 F and +10 F within the interior cavity, causes leaves, branches, and plant matter which are attached to the bud or flower to freeze and become brittle. Concurrently, ice crystals formed as the gas is emitted from the jets, strikes and contacts against portions of the buds or flowers through the openings in the sidewall of the drum. The impacts from these ice crystal contacts causes leaves and branches and unwanted plant matter to fracture, and fall as debris, into a bottom area of the internal cavity of the hopper. Once the process is completed, after a user-determined time period, the debris may be removed through an opening at the bottom of the interior cavity.

The drum is preferably removable from the interior cavity of the hopper. This is accomplished by positioning exterior axles extending from both ends of the drum, upon power driven wheels on both sides of the interior cavity.

In use, in order to maximize particulate and leaf removal from the flowers and buds, it is preferred that the drum be loaded such that the interior area of the drum is between ¼ to ⅓ full. Thus the volume of buds and material deposited to the interior of the drum will be within this range preferably. To that end, a door formed in the sidewall of the drum, may include a measuring area between the sidewall of the drum forming the door, and a secondary wall. The volume of this measuring area will be within the desired range noted. It may be filled while the door of the drum is opened, an will deposit such into the drum once rotation starts.

With respect to the above description, before explaining at least one preferred embodiment of the herein cryo device and method for processing buds and flowers, in detail, it is to be understood that the invention is not limited in its application to the details of construction and to the arrangement of the components in the following description or illustrated in the drawings. The invention herein described and shown is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other cryo tumblers for buds and flowers, and for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. The term "substantially" when employed herein, means plus or minus 20 percent, unless otherwise designated in range.

It is an object of the present invention to provide device and method to enhance the trimming of buds and flowers such as those from *cannabis* and other flowering plants.

It is an additional object of this invention to provide such a trimming device which employs cold temperatures and ice crystal blasting to remove leaves and particulate from the processed buds and flowers.

These and other objects, features, and advantages of the present device and method of cryo processing of buds and flowers, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF DRAWING FIGURES

The accompanying drawings, which are incorporated herein and form a part of the specification, illustrate some, but not the only or exclusive examples of embodiments and/or features of the disclosed system and method herein. It is intended that the embodiments and figures disclosed herein are to be considered illustrative of the invention herein, rather than limiting in any fashion.

DETAILED DESCRIPTION OF THE INVENTION

Figure 1:
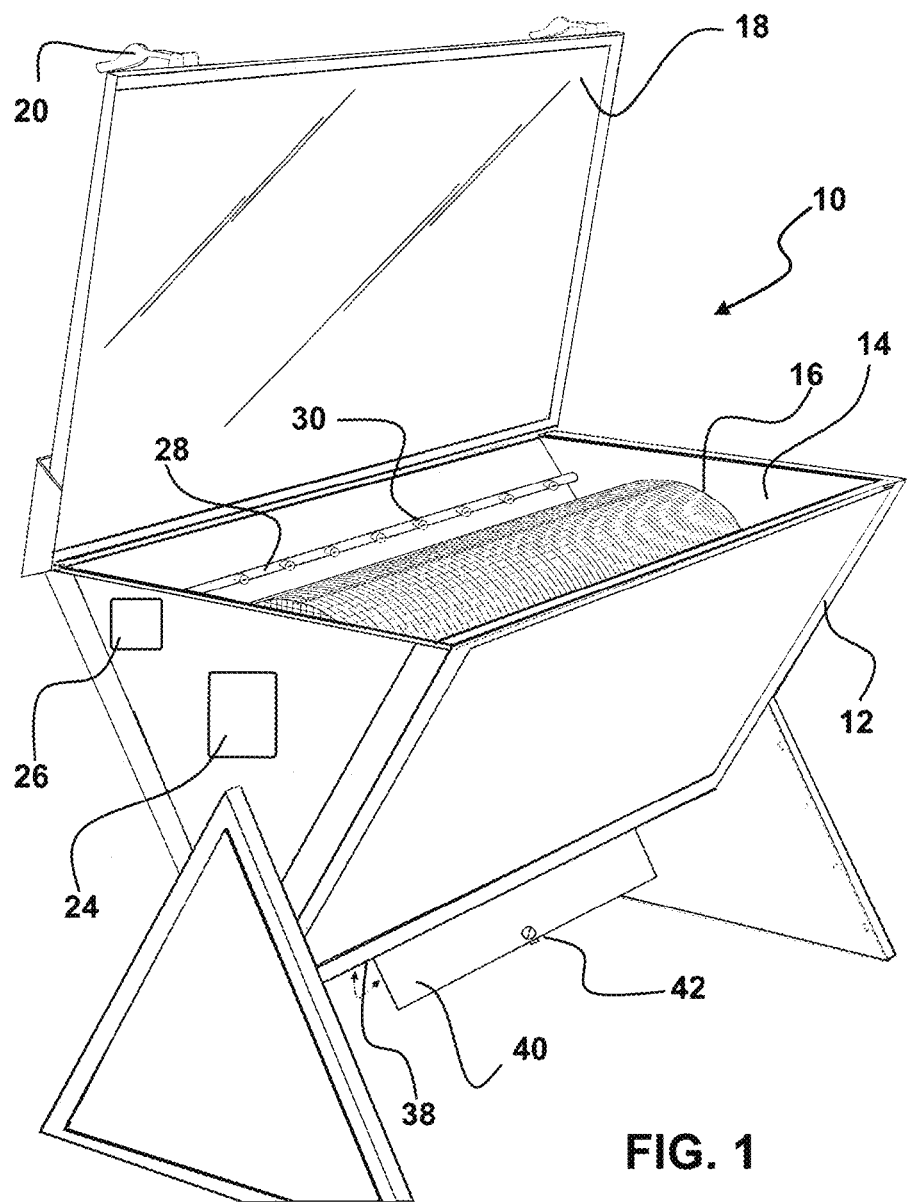
FIG. 1 depicts a view of the hopper device herein having a door in an open position allowing insertion and removal of a drum into an interior cavity of the hopper.

In this description, the directional prepositions of up, upwardly, down, downwardly, front, back, top, upper, bottom, lower, left, right and other such terms refer to the device as it is oriented and appears in the drawings and are used for convenience only and such are not intended to be limiting or to imply that the device has to be used or positioned in any particular orientation.

Now referring to drawings in FIGS. 1-5 wherein similar components are identified by like reference numerals, there is seen in FIG. 1, the device 10 herein, which as shown, or in similar configuration enables the method herein of processing plant flowers and buds for removal of leaves, plant matter, and particulate therefrom.

In FIG. 1 is shown a perspective view of the device 10 showing the hopper 12 having an interior cavity 14 in which a drum 16 is positioned either permanently, or more preferably in a removable engagement. The ability to remove the drum 14 subsequent to processing makes it easier to remove buds and flowers therefrom once cleaned, and such a positioning as described below, is preferred.

A cover 18 is shown raised thereby rendering the hopper 12 to an open position as shown in FIG. 1. Lowering the cover 18 to a substantially sealed engagement with the hopper opening 36 which provides access to the interior cavity 14, transforms the hopper 12 to a sealed configuration shown in FIG. 2. Latches 20 or similar connectors can be employed to hold the 18 cover to the closed position.

Additionally shown in FIG. 1, are a motor 24 having a controller for adjusting the RPM's thereof during use. A pressurized gas supply 26 is in sealed communication with a conduit 28 having a plurality of jets 30 which runs along a line substantially parallel to the sidewall 32 of the circular drum 16. Currently, pressurized carbon dioxide is preferred for the gas supply 26 as it has been shown in experimentation to both freeze the leaves, plant matter, and particulate to be removed quickly, and to form ice crystals upon exit from the jets 30 which impact the leaves and plant matter and particulate adhered to the flowers and buds 34 (FIG. 5), through openings 36 (FIG. 5) in the sidewall 32 of the drum 16.

Additionally shown in FIG. 1, is a lower opening 38 which is accessible by opening a lower door 40 at the bottom side of the hopper 12. Such allows leaves, stems, plant matter, and particulate, removed from the buds 34 by the impact of ice crystals from the jets 30 upon the gas-chilled buds 34, from the interior cavity 14 after processing is complete. This lower door 40 may be closed and locked using a fastener 42 adapted for such.

With the hopper 12 in the open position as in FIG. 1, the drum 16 may be loaded with buds 34 for processing. This may be done by removal of the drum 16 if removably engaged within the interior cavity 14 as preferred herein. If permanently engaged therein, a drum door 44 may be unlocked and opened as in FIGS. 3-4, to allow such loading and removal of material to be processed.

Figure 2:
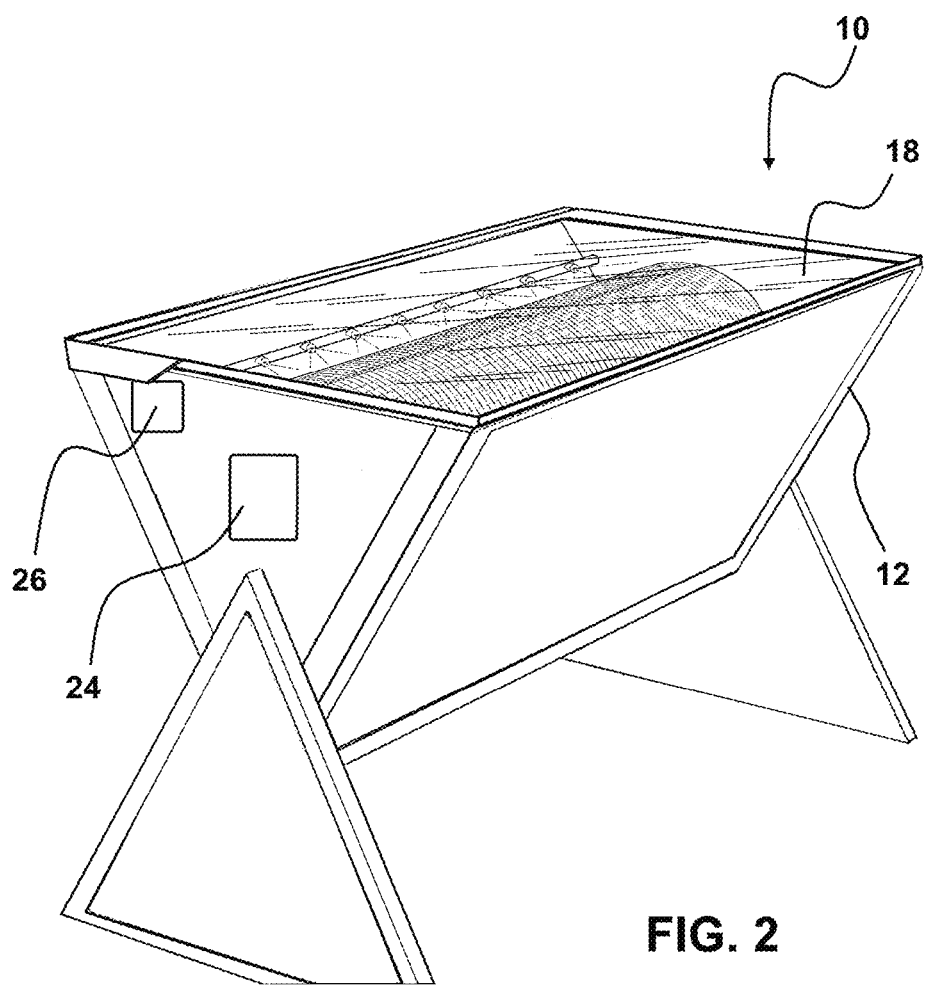
FIG. 2 shows the device herein with the hopper in a closed position, substantially sealing the interior cavity of the hopper from the exterior atmosphere.

As noted FIG. 2 shows the device 10 herein with the hopper 12 in the closed position, during the method of processing the buds 34 or flowers loaded into the internal cavity 46 of the drum 12. In the method of processing herein, the drum 12 is loaded with buds 34 and plant material substantially equal in volume to ¼ to ½ of the volume of the internal cavity 46 of the drum 16.

Once so loaded, the hopper is moved to the closed position of FIG. 2, and the motor 24 is energized to rotate the drum 16 between 40-60 RPM's. With the hopper 12 closed, the pressurized gas supply 26 is connected to the conduit 28 supplying the jets 30 by activation of a valve (not shown but well known).

The gas emitted by the jets 30 freezes the buds 34 and material attached thereto, and ice crystals formed by the carbondioxide or other gas exiting the jets 30 impacts the buds 34 through the openings 36 in the sidewall 32 of the drum 16.

The process can be timed for a desired duration of time, for example between 1 minute and 30 minutes depending on the user requirements, and may be viewed through the clear cover 18.

Figure 3:
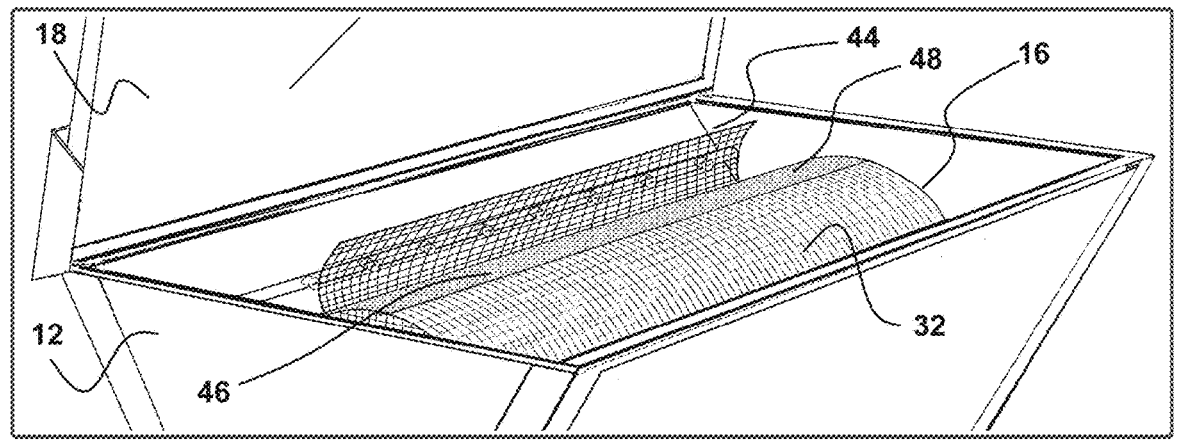
FIG. 3 shows the hopper in the open position, and showing the drum door in an open position.

FIG. 3 shows the hopper 12 in the open position of FIG. 1. Also shown are the drum door 44 opened to allow loading of buds 34 and plant material into the internal cavity 46 of the drum 16 through the drum opening 48. As noted, where the drum 16 is removable from the interior cavity 14 of the hopper 12, this loading and unloading can be accomplished with the drum 16 outside the cavity.

Figure 4:
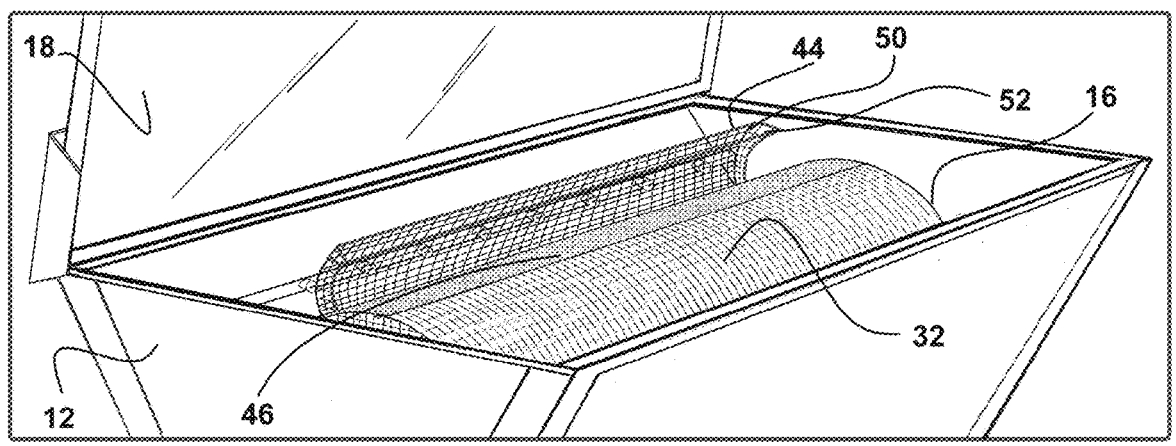
FIG. 4 shows the device as in FIG. 3, but also depicts a volume measuring area formed by a secondary wall engaged to the door portion of the drum.

FIG. 4 shows the device as in FIG. 3, but also depicts a volume measuring area 50 formed by a space between the drum door 44 and a secondary wall 52 engaged to the drum door 44. This measuring area 50 can be formed to hold a desired volume of buds 34 and plant material and thus measure the amount loaded to the internal cavity 46 of the drum 16 when the drum door 44 is opened. Once the drum door 44 is closed and locked with a fastener adapted for such, the material loaded to the volume measuring area 50 will fall into the internal cavity 46 of the drum 16 and be held against the sidewall 32 by centrifugal force of the rotation of the drum 16 by the motor 24.

Figure 5:
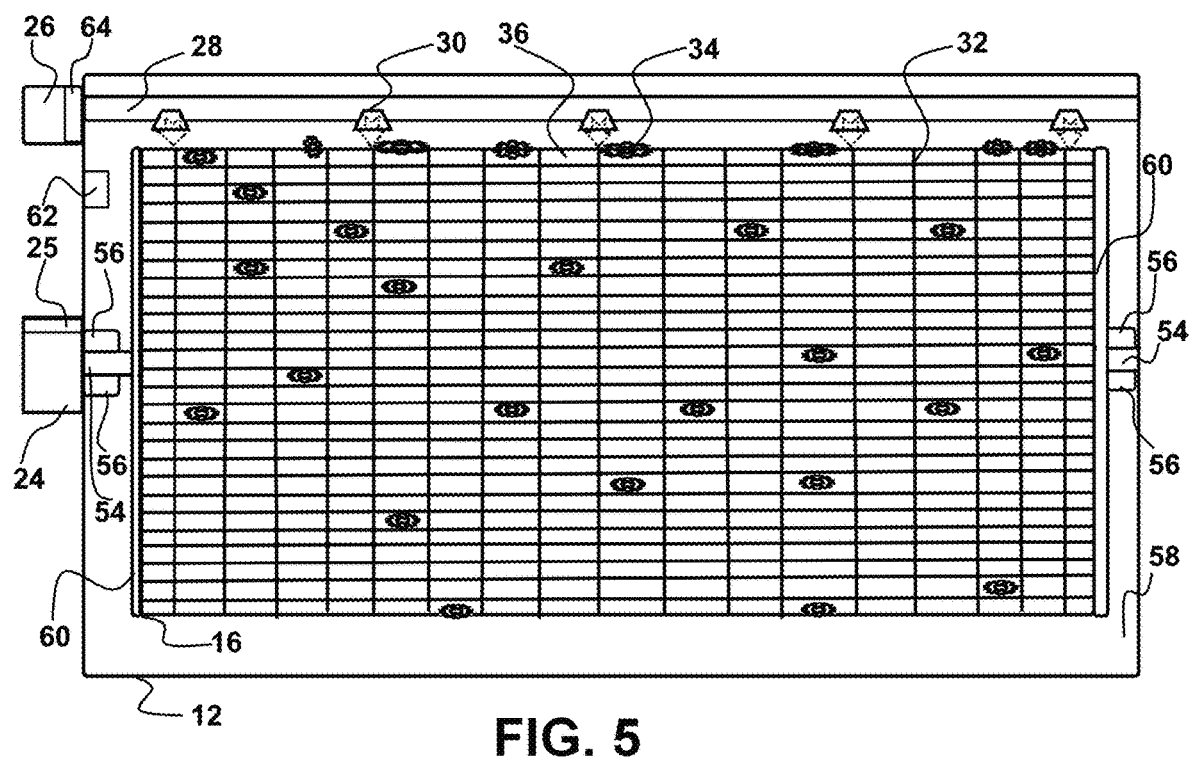
FIG. 5 is an overhead view of the drum operatively engaged with a motor within the interior cavity of the hopper, showing the jets positioned along a line parallel to the sidewall of the rotating drum, and showing the projecting axles on the ends of the drum which may be positioned atop a powered wheel engaged to the motor.

Shown in FIG. 5, is an overhead view of the drum 16 operatively engaged with a motor 24. As shown, the drum 16 is removable and has axles 54 sitting atop adjacent rollers 56 attached to the interior wall 58 surrounding the interior cavity 14. In this removable configuration, the motor 24 is engaged to one or both rollers 56 adjacent the endwall 60 of the drum 16 closest to the motor 24. The endwalls 60 are preferably solid and have no openings 36 therein so that the buds 34 do not catch on the endwalls.

Also shown is the conduit 28 carrying the gas to the jets 30 running along a line substantially parallel to the surface of the sidewall 32 of the circular drum 16. The jets 30 are preferably positioned at a space between inch to 12 inches from the sidewall 32 to allow for freezing of the material within the internal cavity 46, and for ice crystals to form in the gap and thereafter strike the buds 34 during processing.

Additionally shown are a thermocouple 62 which can control the flow and volume of gas from the gas supply 26 through a valve 64 actuated by the signals from the thermocouple 62. A motor controller 25 may also be connected to a speed sensor 27 to control the rotational speed of the drum 16.

In a method of processing flowers and buds 34 from plants, using the device 10 herein or a similar device 10, the buds 34 with plant matter and leaves are loaded into the internal cavity 46 of a rotating drum 16 having openings 36 formed in a sidewall 32 defining the drum 16. Thereafter the drum 16 is rotated and carbon dioxide is communicated to jets 30 positioned along a line parallel or at least adjacent the sidewall 32 for a duration of time allowing ice crystals formed by the exhausting gas from the jets 30 to impact the buds 34 in the rotating drum 16, to thereby allow the impacts of the ice crystals to clean the buds of leaves, plant matter, and particulate.

It should be noted that any of the different depicted and described configurations and components and steps of the cryo processing device and method herein, can be employed with any other configuration or component shown and described as part of the device herein. Additionally, while the present invention has been described herein with reference to particular embodiments thereof and/or steps in the method of production or use, a latitude of modifications, various changes and substitutions are intended in the foregoing disclosure, and it will be appreciated that in some instance some features, or configurations, of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

What is claimed is:

1. An apparatus for removing leaves and plant matter from plant flowers and buds, comprising:
   a hopper, having an interior cavity, said interior cavity accessible from a hopper opening;
   a lid, said lid having a closed position covering said hopper opening and having an open position;
   a drum, said drum rotationally engaged within said interior cavity of said hopper;
   a motor for imparting a rotation to said drum;
   a plurality of jets positioned in said interior cavity of said hopper;
   said plurality of jets exhausting a gas stream from a pressurized gas supply connected thereto, into said interior cavity of said hopper;
   said drum having a sidewall surrounding an internal cavity thereof, said sidewall extending between a first endwall and a second endwall, said sidewall having openings therein;
   a drum door positioned in said sidewall, said drum door having an open position providing access to a drum opening and having a closed position sealing said drum opening;
   said internal cavity of said drum configured for positioning of a volume of plant buds to be cleaned of leaves and stems and plant matter engaged therewith;
   said gas stream exhausted into said interior cavity of said hopper during said rotation of said drum, being at a temperature forming ice crystals upon contact with the air within said interior cavity, which communicate through said openings of said sidewall surrounding said internal cavity and into contacts with said plant buds; and
   said contacts causing a removal of said leaves and stems from said plant buds, whereby said leaves and stems so removed communicate through said openings in said sidewall to a collection area therefor in a lower end of said interior cavity of said hopper.

2. The apparatus for removing leaves and plant matter from plant flowers and buds of claim 1, additionally comprising:
   said openings in said sidewall of said drum having a diameter sized substantially between ¼ inch to ½ of an inch.

3. The apparatus for removing leaves and plant matter from plant flowers and buds of claim 2, additionally comprising:
   a temperature sensor for monitoring a current temperature within said internal cavity;
   a controller receiving a signal of said current temperature within said internal cavity; and
   said controller regulating said pressurized gas supply communicated to said jets to maintain said current temperature within said internal cavity to said current temperature which is substantially between −10 F and +10 F.

4. The apparatus for removing leaves and plant matter from plant flowers and buds of claim 3, additionally comprising:
   a speed sensor for monitoring a rotational speed of said drum; and
   said speed sensor adjusting a rotation speed of said motor to maintain said rotational speed of said drum to substantially 30 to 90 revolutions thereof per minute.

5. The apparatus for removing leaves and plant matter from plant flowers and buds of claim 4, additionally comprising:
   said drum door having a measuring area therein for measuring said volume of plant buds for deposit within said internal cavity.

6. The apparatus for removing leaves and plant matter from plant flowers and buds of claim 2, additionally comprising:
   a speed sensor for monitoring a rotational speed of said drum; and
   said speed sensor adjusting a rotation speed of said motor to maintain said rotational speed of said drum to substantially 30 to 90 revolutions thereof per minute.

7. The apparatus for removing leaves and plant matter from plant flowers and buds of claim 6, additionally comprising:
   said drum door having a measuring area therein for measuring said volume of plant buds for deposit within said internal cavity.

8. The apparatus for removing leaves and plant matter from plant flowers and buds of claim 2, additionally comprising:
   said drum door having a measuring area therein for measuring said volume of plant buds for deposit within said internal cavity.

9. The apparatus for removing leaves and plant matter from plant flowers and buds of claim 1, additionally comprising:
   a temperature sensor for monitoring a current temperature within said internal cavity;
   a controller receiving a signal relative to said current temperature within said internal cavity; and
   said controller regulating said pressurized gas supply communicated to said jets to maintain said current temperature within said internal cavity to said current temperature which is substantially between −10 F and +10 F.

10. The apparatus for removing leaves and plant matter from plant flowers and buds of claim 9, additionally comprising:
    a speed sensor for monitoring a rotational speed of said drum; and
    said speed sensor adjusting a rotation speed of said motor to maintain said rotational speed of said drum to substantially 30 to 90 revolutions thereof per minute.

11. The apparatus for removing leaves and plant matter from plant flowers and buds of claim 10, additionally comprising:
    said drum door having a measuring area therein for measuring said volume of plant buds for deposit within said internal cavity.

12. The apparatus for removing leaves and plant matter from plant flowers and buds of claim 9, additionally comprising:
    said drum door having a measuring area therein for measuring said volume of plant buds for deposit within said internal cavity.

13. The apparatus for removing leaves and plant matter from plant flowers and buds of claim 1, additionally comprising:
    a speed sensor for monitoring a rotational speed of said drum; and
    said speed sensor adjusting a rotation speed of said motor to maintain said rotational speed of said drum to substantially 30 to 90 revolutions thereof per minute.

14. The apparatus for removing leaves and plant matter from plant flowers and buds of claim 13, additionally comprising:

said drum door having a measuring area therein for measuring said volume of plant buds for deposit within said internal cavity.

15. The apparatus for removing leaves and plant matter from plant flowers and buds of claim 1, additionally comprising:

said drum door having a measuring area therein for measuring said volume of plant buds for deposit within said internal cavity.

\* \* \* \* \*